(12) United States Patent
Wirth et al.

(10) Patent No.: US 7,587,925 B2
(45) Date of Patent: Sep. 15, 2009

(54) METHOD FOR OPERATING A SENSOR FOR RECORDING PARTICLES IN A GAS STREAM AND DEVICE FOR IMPLEMENTING THE METHOD

(75) Inventors: Ralf Wirth, Farmington Hills, MI (US); Heribert Haerle, Kornwestheim (DE); Torsten Handler, Stuttgart (DE); Dirk Samuelsen, Ludwigsburg (DE); Werner Christl, Moeglingen (DE); Sabine Rösch, Ditzingen (DE); Bernhard Kamp, Ludwigsburg (DE); Michael Kolitsch, Weissach (DE); Katharina Schaenzlin, Rottenburg-Obernau (DE)

(73) Assignee: Robert Bosch GmbH, Stuttgart (DE)

( * ) Notice: Subject to any disclaimer, the term of this patent is extended or adjusted under 35 U.S.C. 154(b) by 352 days.

(21) Appl. No.: 11/510,198

(22) Filed: Aug. 25, 2006

(65) Prior Publication Data
US 2007/0089478 A1     Apr. 26, 2007

(30) Foreign Application Priority Data
Aug. 29, 2005   (DE) ................ 10 2005 040 790

(51) Int. Cl.
*G01N 15/06* (2006.01)
(52) U.S. Cl. .................. 73/1.02; 73/1.06; 73/1.16; 73/23.33; 73/28.01; 73/31.03
(58) Field of Classification Search ............ 73/23.2, 73/23.21, 23.33, 28.01–28.06, 31.03, 1.02, 73/1.06, 1.07, 1.16, 1.34
See application file for complete search history.

(56) References Cited

U.S. PATENT DOCUMENTS

| | | | | |
|---|---|---|---|---|
| 4,163,433 A | * | 8/1979 | Fujishiro | 123/687 |
| 4,841,157 A | * | 6/1989 | Downing, Jr. | 250/574 |
| 5,424,558 A | * | 6/1995 | Borden et al. | 250/573 |
| 5,444,974 A | * | 8/1995 | Beck et al. | 60/274 |
| 5,592,296 A | * | 1/1997 | Pye | 356/435 |
| 5,964,089 A | * | 10/1999 | Murphy et al. | 60/286 |
| 6,036,827 A | * | 3/2000 | Andrews et al. | 204/252 |
| 6,167,107 A | * | 12/2000 | Bates | 377/10 |
| 6,539,707 B2 | * | 4/2003 | Ikemoto et al. | 60/285 |
| 6,611,611 B2 | * | 8/2003 | Oka et al. | 382/110 |

(Continued)

FOREIGN PATENT DOCUMENTS

DE   101 33 384   1/2003

(Continued)

*Primary Examiner*—David A. Rogers
(74) *Attorney, Agent, or Firm*—Kenyon & Kenyon LLP

(57) ABSTRACT

A method for operating a sensor for recording particles in an exhaust gas flow and a device for carrying out the method are provided, in which at least one measure of the exhaust gas flow is ascertained and in which the measure of the exhaust gas flow is taken into consideration in the valuation of the particle sensor signal made available by the particle sensor. The procedure is based on the knowledge that the exhaust gas flow, for instance, the exhaust gas volume flow, has an influence on the particle sensor signal made available by the particle sensor, especially when the measuring effect is based on the depositing of particles on a sensor surface. Using the procedure, a possibly present cross sensitivity of the particle sensor with respect to different exhaust gas flows is taken into consideration, so that the measuring accuracy is increased.

20 Claims, 2 Drawing Sheets

U.S. PATENT DOCUMENTS 7,064,562 B2 * 6/2006 Lin et al. .................... 324/698
7,299,683 B2 * 11/2007 Nikkels et al. ............. 73/53.07
2006/0156791 A1 * 7/2006 Tikkanen et al. ........... 73/23.33
2007/0209427 A1 * 9/2007 Nikkels et al. ............. 73/61.71

FOREIGN PATENT DOCUMENTS

DE  101 33 385  1/2003

* cited by examiner

METHOD FOR OPERATING A SENSOR FOR RECORDING PARTICLES IN A GAS STREAM AND DEVICE FOR IMPLEMENTING THE METHOD

FIELD OF THE INVENTION

The present invention relates to a method for operating a sensor for detecting particles in a gas stream and a device for implementing the method.

BACKGROUND INFORMATION

For monitoring and, if necessary, controlling the combustion properties in combustion processes, there is a need for recording at least one measure of the particle concentration in the exhaust gas of combustion processes. In particular, there is a need for recording at least one measure for the particle concentration in the exhaust gas of internal combustion engines, especially Diesel internal combustion engines.

The term particle concentration is mirrored in the following with the same meaning as particle mass or particle quantity. Reference will only still be made to particle mass. If the combustion process occurs in an internal combustion engine, which is preferably situated in a motor vehicle, what is of interest is the particle mass or the particle quantity which has been obtained on a predefined path.

A particle sensor has become known, for example, from German Patent Application No. DE 101 33 385, which includes a collecting chamber that is able to be connected to an exhaust gas stream of an internal combustion engine. On the upper side of the collecting chamber there is situated a first electrode. At the lower side, that is, opposite the first electrode, a second electrode is situated. The collecting chamber between the two electrodes is hollow. When the known sensor is in operation, particles, especially soot particles, arrive in the collecting chamber and deposit in the hollow space between the two electrodes. The at least slightly conductive particles bridge the intervening space between the two electrodes, so that there is a change in the impedance of the particle sensor. The impedance or the change with time of the impedance may be valued, and it is a measure for the load or the increase in load of the particle sensor with particles. Since the measuring effect is based on a collection of particles, the particle sensor may be designated as an integrating particle sensor.

Another particle sensor is described in German Patent Application No. DE 101 33 384. In this particle sensor the two electrodes are situated on one side of a collecting chamber, and mate in the shape of a comb. In this integrating particle sensor, too, the impedance and/or its change between the two electrodes may be drawn upon as a measure for the particle mass in the exhaust gas that has appeared on the path in a predefined time.

With the aid of experiments, it has turned out that the known particle sensors, especially the integrating particle sensors, for instance, resistive particle sensors, have cross sensitivities which, when there is a change in the conditions of the combustion process, may lead to influencing the particle sensor signal.

SUMMARY OF THE INVENTION

The present invention is based on increasing the measuring accuracy of particle sensors, especially of integrating particle sensors.

The method according to the present invention, for operating a sensor for recording particles in an exhaust gas stream, provides that at least one measure for the exhaust gas stream at the particle sensor is ascertained, and that the measure for the exhaust gas stream is taken into consideration in the valuation of the particle sensor signal made available by the particle sensor.

The procedure according to the present invention is based on the knowledge that the exhaust gas stream has an influence on the particle sensor signal made available by the particle sensor, especially when the sensor effect is based on the depositing of particles on a sensor surface. Using a procedure according to the present invention, a possibly present cross sensitivity of the particle sensor with respect to different exhaust gas streams is taken into consideration, so that the measuring accuracy is increased.

With the aid of experiments, it was established that a greater exhaust gas stream makes the depositing of particles on the surface of the particle sensor more difficult. According to one embodiment it may therefore be provided that, in the case of a growing exhaust gas stream, an increase in sensor sensitivity is provided, in order to compensate for the decreasing sensitivity. In the case of an integrated particle sensor, that is, a particle sensor in which the measuring effect is based, for example, on the depositing of particles on a sensor surface, the adjustment of the sensor sensitivity may be undertaken by influencing a threshold value to which the particle sensor signal is compared. Since a growing exhaust gas stream generally means, in the case of an integrated particle sensor, a reduction in the sensor's sensitivity, a lowering of the threshold value may be undertaken in response to such a sensor.

The term exhaust gas stream may mean an exhaust gas mass flow, an exhaust gas volumetric flow or even a particle flow, particles being able to be solid or gaseous. In this instance, the exhaust gas volumetric flow may be calculated from the exhaust gas mass flow and from a determined measure for the exhaust gas temperature.

According to one embodiment it is provided that the measure for the exhaust gas flow is ascertained from an air signal, that is recorded in an air intake region of the combustion process, and from a fuel signal which is at least a measure for the fuel quantity supplied for the combustion process. According to one alternative embodiment it is provided that the measure for the exhaust gas flow is recorded in an air intake region of the combustion process and is ascertained from an air ratio lambda, which is recorded in the exhaust gas of the combustion process.

The device according to the present invention, for operating a sensor for recording particles in a gas stream, relates first of all to a control unit which is specially prepared for carrying out the method. The control unit preferably includes at least one electrical memory in which the method steps are stored in the form of a computer program.

A further refinement of the device according to the present invention provides that an integrating particle sensor, for example, a resistive particle sensor, is provided as the particle sensor. One embodiment provides that the particle sensor includes means for recording a measure for the temperature of the particle sensor, which may be drawn upon at least in certain operating states of the particle sensor as a measure for the exhaust gas temperature.

As the means for recording the temperature, a sensor heater may be provided, for example, which may be required for the periodic burning off of the inserted particles. What can be provided is, for example, a valuation of the electrical resistance of the sensor heater during an operating pause of the sensor heater, it being assumed that the resistance reflects at least a measure for the exhaust gas temperature. If necessary, the sensor element of the particle sensor may itself be drawn upon as temperature sensor.

DETAILED DESCRIPTION

Figure 1:
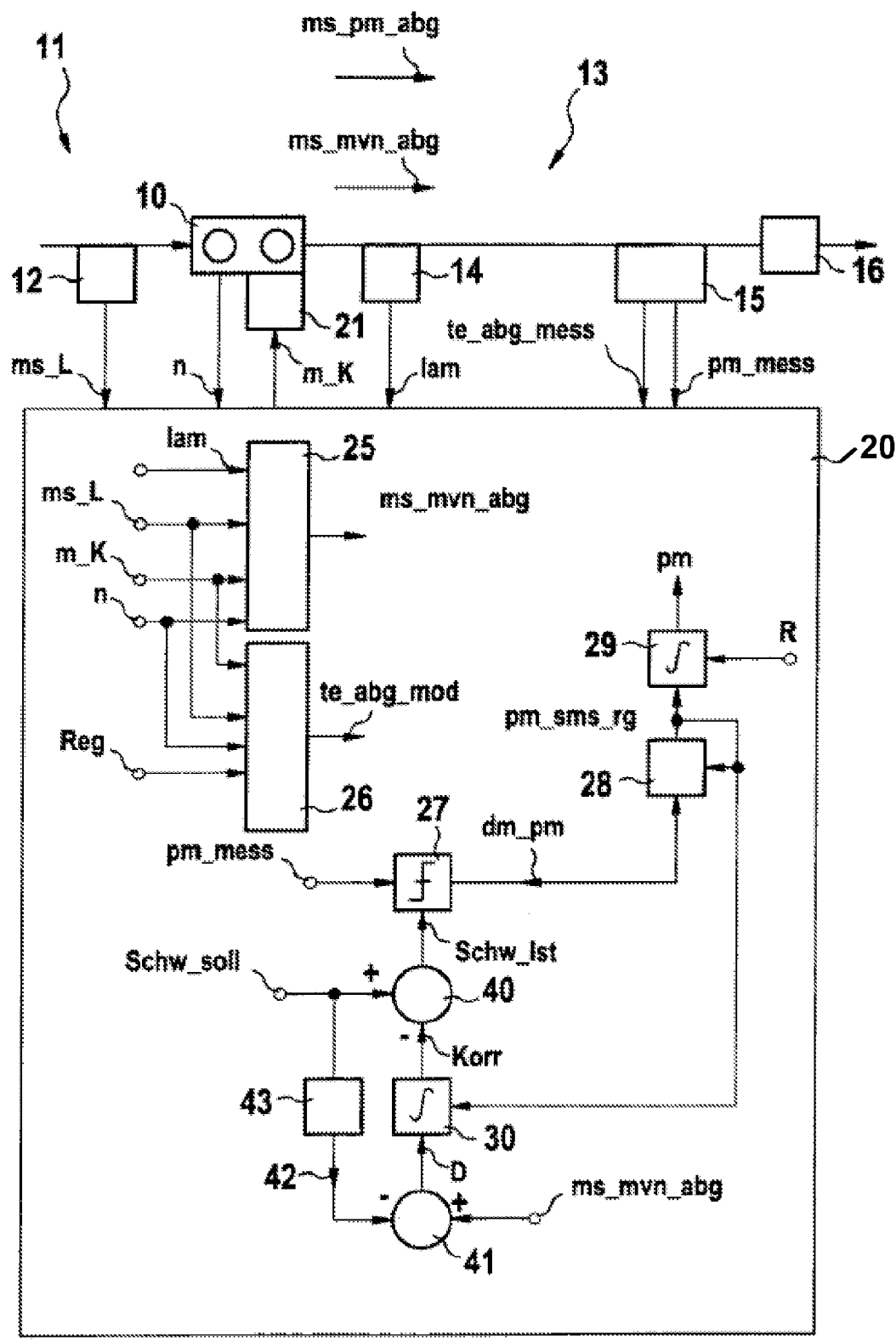
FIG. 1 shows a technical environment in which a method according to the present invention is performed, as well as a block diagram of a part of a control unit.

FIG. 1 shows an internal combustion engine 10, in whose air intake region 11 an air detection 12 is situated, and in whose exhaust gas region 13 a lambda sensor 14, a particle sensor 15 and an exhaust gas treatment device 16 are situated.

Air detection 12 sends an air signal ms_L to a control unit 20 internal combustion engine 10 sends a rotation signal n, lambda sensor 14 sends a lambda signal lam and particle sensor 15 sends both a particle sensor signal pm_mess and a particle sensor temperature signal te_abg_mess. Control unit 20 sends a fuel signal m_K to a fuel-metering device 21.

An exhaust gas stream ms_mvn_abg and a particle stream ms_mm_abg appear in exhaust gas region 13.

Control unit 20 includes an exhaust gas ascertainment 25, to which lambda signal lam, air signal ms_L, fuel signal m_K as well as rotation signal n are made available, and which makes available exhaust gas flow ms_mvn_abg.

Control unit 20 also includes an exhaust gas ascertainment 26, to which are made available air signal ms_L, fuel signal m_K, rotation signal n as well as a regeneration signal Reg, and which makes available a computed exhaust gas temperature te_abg_mod.

Particle sensor signal pm_mess that is made available by particle sensor 15 arrives at a comparator 27, which compares particle sensor signal pm_mess to a threshold actual value Schw_lst, and which makes available a difference particle signal dm_pm to a timing device 28. Timing device 28 prepares a particle sensor regeneration signal pm_sens_reg, which is made available to a first integrator 29, to the timing device 28 itself and to a second integrator 30. First integrator 29, to which a reset signal R is also made available, makes available a particle signal pm.

Threshold actual value Sch_lst is made available by a first difference determination 40, to which a threshold setpoint value Schw_Soll and a correction signal Korr are made available. Correction signal Korr is prepared by second integrator 30 as a function of particle sensor regeneration signal pm_sens_reg as well as a function of a difference signal D. Difference signal D makes available a second difference determination 41 as a function of exhaust gas flow ms_mvn_abg and of a converted threshold setpoint value 42, which makes available a conversion 43 as a function of threshold setpoint value Schw_Soll.

Figure 2:
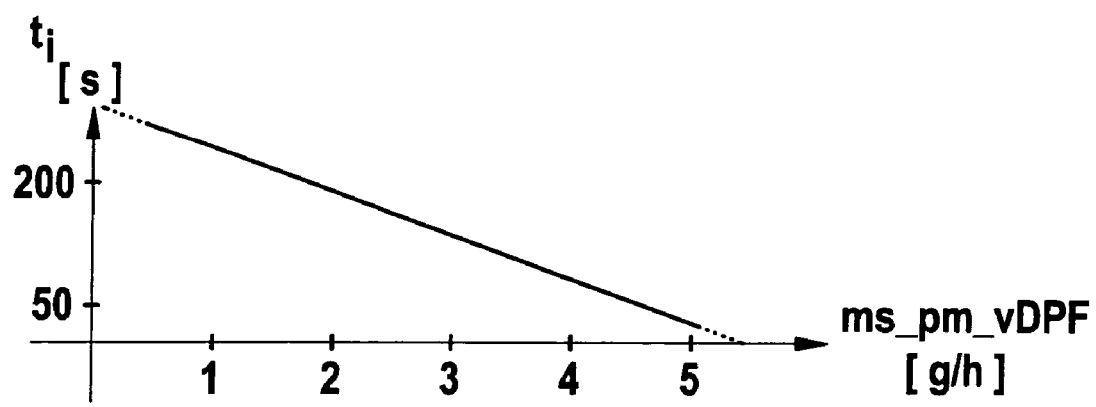
FIG. 2 shows a relationship between a measuring time of a particle sensor and a particle stream.

FIG. 2 shows a relationship between particle flow ms_pm_abg and a measuring time ti ascertained by timing device 28. Particle flow ms_pm_abg may be given, for example, in the unit grams/hour [g/h] and measuring time ti in the unit of seconds [s].

The method operates as follows:

The exemplary embodiment shown is based on equipment having an internal combustion engine, in whose exhaust gas region 13 exhaust gas stream ms_mvn_abg appears. Internal combustion engine 10 is only one example of a combustion process in whose exhaust gas region 13 exhaust gas flow ms_mvn_abg appears. Besides exhaust gas flow ms_mvn_abg, at least particle flow ms_pm_abg appears. For emission control, exhaust gas treatment device 16 is provided which, for example, may include at least one catalytic converter and/or at least one particulate filter.

Particle flow ms_pm_abg is recorded by particle sensor 15. In the case of particle sensor 15, a sensor may be involved whose particle sensor signal pm_mess directly reflects a measure of the concentration of particles in exhaust gas region 13. In the following, it is assumed that particle sensor 15 is an integrating particle sensor which, for example, is designed as a resistive particle sensor according to the related art mentioned at the outset. In such a sensor, the particles are deposited on the sensor surface, and collected up to a prespecified threshold value—threshold setpoint value Schw_Soll. Thereafter, particle sensor 15 is reset to its initial state, for instance, by burning off the particles.

The collected particles influence the conductivity of the sensor, so that particle sensor signal pm_mess reflects a measure for the particle mass or the particle quantity in a predefined time span, in the following, only the term particle mass still being used, and, provided particle sensor 15 is situated in a motor vehicle, particle sensor signal pm_mess may be regarded as a measure for the particle mass with reference to a travel path.

The relationship between particle flow ms_pm_abg and time ti ascertained by timing device 28 is shown in greater detail in FIG. 2, an integrating particle sensor 15 being assumed. The particle sensor begins with the depositing of the particles starting from a particle sensor regeneration signal pm_sens_reg that has appeared, which transfers particle sensor 15 to an output state. The time during the depositing is recorded by timing device 28, which is stopped by the appearance of difference particle signal dm_pm. After the stopping of timing device 28, determined time ti is fixed. Difference particle signal dm_pm is made available by comparator 27 if particle sensor signal pm_mess exceeds threshold actual value Schw_lst. Threshold actual value Schw_lst corresponds to a maximum loading of particle sensor 15, at the exceeding of which particle sensor 15 has to be regenerated, for example, by burning off.

It is provided, according to the present invention that exhaust gas flow ms_mvn_abg shall be taken into consideration in the valuation of particle sensor signal pm_mess made available by the particle sensor. It was determined experimentally that particle flow ms_pm_abg may have an influence on particle sensor signal pm_mess, particularly if an integrating particle sensor 15 is involved. It is assumed that procedures in a boundary layer on the surface of the particle sensor make a difference, at a greater exhaust gas flow ms_mvn_abg, as seen relatively, fewer particles being deposited than at a lower exhaust gas flow ms_mvn_abg.

In the exemplary embodiment shown, the sensitivity of particle sensor 15 and the valuation of particle sensor signal pm_mess made available by particle sensor 15 are influenced in that threshold setpoint value Schw-Soll, to which particle sensor signal pm_mess is compared in comparator 27, is corrected by correction signal Korr as a function of exhaust gas flow ms_mvn_abg. In the exemplary embodiment shown, the procedure is such that threshold setpoint value Schw_Soll is modified by correction signal Korr in first difference determination 40 so as to obtain threshold actual value Schw_lst. In case of a great exhaust gas flow ms_mvn_abg, there is a reduction in threshold actual value Schw_lst, in order to increase the sensitivity of particle sensor 15, since at a high exhaust gas flow ms_mvn_abg, as seen relatively, for example, fewer particles are deposited than at a low exhaust gas flow ms_mvn_abg.

Correction signal Korr is made available by second integrator 30 as a function of difference D, which appears between converted threshold setpoint value 42 and exhaust gas flow ms_mvn_abg, and which is ascertained by second difference determination 41. Because of the described procedure using second difference determination 41 and second integrator 30, correction signal Korr may accept both positive and negative values. Second integrator 30 is provided, because the exemplary embodiment is supposed to be based on integrating particle sensor 15, and, during measuring time ti ascertained by timing device 28, different exhaust gas flows ms_mvn_abg may appear, whose influence should also be taken integrally into consideration.

Measuring time ti ascertained from timing device 28 is already, in principle, a measure of the particle mass recorded by particle sensor 15. In practice, the recording of a substantially greater particle mass may be desired than particle sensor 15 is in a position to record, and when this is achieved, certain measures are to be taken up.

Such a measure is, for example, a regeneration of a particulate filter which may be included in exhaust gas treatment device 16. Another measure provides, for example, a diagnosis or the determination of the particle mass with reference to a predefined time or with reference to a predefined path. After the exceeding of a predefined particle mass, one may arrange, for instance the making available of an error signal or a warning message.

There are therefore operating cases in which more than one measuring cycle of an integrating particle sensor 15 should be provided. The number of cycles is recorded by first integrator 29 which, for example, is implemented as a counter, by summing up the particle regeneration signals om_sens_reg that have occurred.

In exhaust gas flow ms_mvn_abg, for instance, the exhaust gas mass flow may be involved. Preferably, exhaust gas volume flow is drawn upon, which is a direct measure for the influencing of particle sensor signal pm-mess. The exhaust gas volume flow may be obtained from the exhaust gas mass flow, by taking the exhaust gas temperature into consideration. In order to record the exhaust gas temperature, a separate exhaust gas temperature sensor may be provided. In the exemplary embodiment shown, the assumption is made that particle sensor 15 has means for recording the temperature of particle sensor 15, so that particle sensor 15 is able to make available particle sensor temperature signal te_abg_mess. Particle sensor temperature signal te_abg_mess may, for example, be obtained from a required sensor heater, by recording the internal resistance of the heating element, so that particle sensor temperature signal te_sens_mess reflects at least a measure of the exhaust gas temperature, especially when the heater is switched off.

Exhaust gas flow ms_mvn_abg is determined by exhaust gas determination 25. The determination may be based on air signal ms_L and fuel signal m_K. Preferably, exhaust gas flow ms_mvn_abg is ascertained from lambda signal lam recorded by lambda sensor 14 and from air signal ms_L. Fuel signal m_K is included indirectly in lambda signal m_K. If necessary, rotation signal n of internal combustion engine 10 may additionally be taken into consideration.

Instead of a measurement of the exhaust gas temperature, a computation or at least an estimate of the exhaust gas temperature may be made. The computation of the exhaust gas temperature takes place in exhaust gas temperature determination 26, which makes available computed exhaust gas temperature signal te_abg_mod as a function of air signal ms_L and of fuel signal m_K. If necessary, rotation signal n may be taken into consideration here too. Furthermore, exhaust gas temperature determination 26 may take into consideration regeneration signal Reg, which appears during the regeneration of a particulate filter included in exhaust gas treatment device 16. If a regeneration signal Reg is present, possibly an increased exhaust gas temperature occurs, the temperature increase being made available either by introducing combustible components into exhaust gas region 13, or by suitable operation of combustion process 10. Regeneration signal Reg may be taken into consideration in exhaust gas temperature determination 26, in order to take into consideration the changed circumstances.

What is claimed is:

1. A method for operating a particle sensor for recording particles in an exhaust gas flow, the method comprising:
    ascertaining at least one measure of the exhaust gas flow at the particle sensor;
    in a valuation of a particle sensor signal made available by the particle sensor, taking into consideration the measure for the exhaust gas flow; and
    in response to an increasing gas flow, providing an increase in a sensor sensitivity.

2. The method according to claim 1, further comprising, in an integrating particle sensor, in the case of an increasing exhaust gas flow, providing a reduction of a threshold setpoint value to a threshold actual value, to which the particle sensor signal is compared.

3. A method for operating a particle sensor for recording particles in an exhaust gas flow, the method comprising:
    ascertaining at least one measure of the exhaust gas flow at the particle sensor; and
    in a valuation of a particle sensor signal made available by the particle sensor, taking into consideration the measure for the exhaust gas flow;
    wherein an exhaust gas mass flow is drawn upon as a measure for the exhaust gas flow.

4. The method according to claim 3, wherein the sensor is an integrating particle sensor.

5. A method for operating a particle sensor for recording particles in an exhaust gas flow, the method comprising:
    ascertaining at least one measure of the exhaust gas flow at the particle sensor; and
    in a valuation of a particle sensor signal made available by the particle sensor, taking into consideration the measure for the exhaust gas flow;
    wherein an exhaust gas volume flow is drawn upon as a measure for the exhaust gas flow.

6. The method according to claim 5, further comprising computing the exhaust gas volume flow from an exhaust gas mass flow and from an ascertained measure of an exhaust gas temperature.

7. The method according to claim 5, wherein the sensor is an integrating particle sensor.

8. A method for operating a particle sensor for recording particles in an exhaust gas flow, the method comprising:
    ascertaining at least one measure of the exhaust gas flow at the particle sensor; and
    in a valuation of a particle sensor signal made available by the particle sensor, taking into consideration the measure for the exhaust gas flow;
    wherein the measure of the exhaust gas flow is ascertained from an air signal, which is recorded in an air intake region of a combustion process, and from a fuel signal, which is at least a measure of a fuel quantity supplied to the combustion process.

9. The method according to claim 8, wherein the sensor is an integrating particle sensor.

10. A method for operating a particle sensor for recording particles in an exhaust gas flow, the method comprising:
- ascertaining at least one measure of the exhaust gas flow at the particle sensor; and
- in a valuation of a particle sensor signal made available by the particle sensor, taking into consideration the measure for the exhaust gas flow;
- wherein the measure of the exhaust gas flow is ascertained from an air signal, which is recorded in an air intake region of a combustion process, and from an air ratio lambda, which is recorded in an exhaust gas region of the combustion process.

11. A device for operating an integrating particle sensor for recording particles in an exhaust gas flow, comprising:
- at least one control unit for performing the following:
  - ascertaining at least one measure of the exhaust gas flow at the integrating particle sensor; and
  - in a valuation of a particle sensor signal made available by the integrating particle sensor, taking into consideration the measure for the exhaust gas flow.

12. The device according to claim 11, wherein, in response to an increasing gas flow, an increase in a sensor sensitivity is provided.

13. The device according to claim 12, wherein, in the integrating particle sensor, in the case of an increasing exhaust gas flow, there is provided a reduction of a threshold setpoint value to a threshold actual value, to which the particle sensor signal is compared.

14. The device according to claim 11, wherein an exhaust gas mass flow is drawn upon as a measure for the exhaust gas flow.

15. The device according to claim 11, wherein an exhaust gas volume flow is drawn upon as a measure for the exhaust gas flow.

16. The device according to claim 15, wherein the exhaust gas volume flow is computed from an exhaust gas mass flow and from an ascertained measure of an exhaust gas temperature.

17. The device according to claim 11, wherein the measure of the exhaust gas flow is ascertained from an air signal, which is recorded in an air intake region of a combustion process, and from a fuel signal, which is at least a measure of a fuel quantity supplied to the combustion process.

18. The device according to claim 11, wherein the measure of the exhaust gas flow is ascertained from an air signal, which is recorded in an air intake region of a combustion process, and from an air ratio lambda, which is recorded in an exhaust gas region of the combustion process.

19. The device according to claim 11, wherein the particle sensor includes means for recording a temperature of the particle sensor which is drawn upon for obtaining at least one measure of an exhaust gas temperature.

20. A device for operating a particle sensor for recording particles in an exhaust gas flow, comprising:
- at least one control unit for performing the following:
  - ascertaining at least one measure of the exhaust gas flow at the particle sensor; and
  - in a valuation of a particle sensor signal made available by the particle sensor, taking into consideration the measure for the exhaust gas flow;
- wherein the particle sensor includes means for recording a temperature of the particle sensor which is drawn upon for obtaining at least one measure of an exhaust gas temperature.

* * * * *

UNITED STATES PATENT AND TRADEMARK OFFICE
CERTIFICATE OF CORRECTION

PATENT NO.       : 7,587,925 B2                    Page 1 of 1
APPLICATION NO.  : 11/510198
DATED            : September 15, 2009
INVENTOR(S)      : Wirth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Twenty-first Day of September, 2010

David J. Kappos
*Director of the United States Patent and Trademark Office*